(12) United States Patent
Grimes et al.

(10) Patent No.: US 8,137,958 B2
(45) Date of Patent: Mar. 20, 2012

(54) ACTIVE GRIP FILTER PLUG FOR SAMPLE COLLECTION DEVICES

(75) Inventors: Eric E. Grimes, Hudson, MA (US);
Steven A. Scampini, Groton, MA (US);
Ryan Oliva, Marlborough, MA (US);
Tuan Ha, Randolph, MA (US)

(73) Assignee: Cytyc Corporation, Marlborough, MA (US)

( * ) Notice: Subject to any disclaimer, the term of this patent is extended or adjusted under 35 U.S.C. 154(b) by 572 days.

(21) Appl. No.: 12/340,132

(22) Filed: Dec. 19, 2008

(65) Prior Publication Data
US 2009/0162930 A1    Jun. 25, 2009

Related U.S. Application Data

(60) Provisional application No. 61/015,655, filed on Dec. 20, 2007.

(51) Int. Cl.
*C12M 1/12* (2006.01)

(52) U.S. Cl. ............... 435/295.3; 435/309.1; 422/74; 73/61.71

(58) Field of Classification Search ............... 435/309.1, 435/295.3; 73/61.71, 864.72; 422/74; 210/197.19, 210/615, 650, 747.3, 780, 295, 323.2, 339; 209/155, 170, 172.5, 185
See application file for complete search history.

(56) References Cited

U.S. PATENT DOCUMENTS

| | | | |
|---|---|---|---|
| 3,927,623 A * | 12/1975 | Caron | 410/112 |
| 4,960,130 A * | 10/1990 | Guirguis | 600/573 |
| 5,074,154 A | 12/1991 | Allen et al. | |
| 5,143,627 A | 9/1992 | Lapidus et al. | |
| 5,240,606 A | 8/1993 | Lapidus et al. | |
| 5,269,918 A | 12/1993 | Lapidus et al. | |
| 5,282,978 A | 2/1994 | Polk, Jr. et al. | |
| 5,364,597 A | 11/1994 | Polk, Jr. et al. | |
| 5,704,803 A * | 1/1998 | Oshima et al. | 439/500 |
| 5,772,818 A | 6/1998 | Polk, Jr. et al. | |
| 5,942,700 A | 8/1999 | Radcliffe et al. | |
| 2004/0140258 A1 | 7/2004 | Jainek et al. | |
| 2005/0247646 A1 | 11/2005 | Linder | |
| 2007/0134134 A1 | 6/2007 | Watts et al. | |

FOREIGN PATENT DOCUMENTS

| | | |
|---|---|---|
| DE | 373665 | 5/1989 |
| EP | 1403573 | 3/2004 |
| GB | 526796 | 9/1940 |
| GB | 1266603 | 3/1972 |
| JP | 11013887 | 1/1999 |

OTHER PUBLICATIONS

PCT International Search Report and Written Opinion for PCT/US2008/087793, Applicant CYTYC Corporation, Forms PCT/ISA/210, 220, and 237 dated May 5, 2009 (15 pages).

* cited by examiner

*Primary Examiner* — William H Beisner
*Assistant Examiner* — Michael Hobbs
(74) *Attorney, Agent, or Firm* — Vista IP Law Group LLP

(57) ABSTRACT

A system for collecting a biological sample includes a collection device comprising a cylindrical body having a bore extending there through and a filter membrane disposed at one end thereof; a filter plug having an insert configured for insertion into the bore; a collar concentrically mounted about the exterior surface of the insert and configured for insertion into the bore; and a gasket disposed about the exterior surface of the insert, wherein an outer dimension of the gasket is variable in response to relative movement between the collar and the insert, and wherein the gasket has a cross section with two end portions and a mid portion that is located radially further away from the insert than the two end portions.

9 Claims, 6 Drawing Sheets

ACTIVE GRIP FILTER PLUG FOR SAMPLE COLLECTION DEVICES

RELATED APPLICATION DATA

This application claims the benefit of U.S. Provisional Patent Application No. 61/015,655, filed on Dec. 20, 2007, the entire disclosure of which is expressly incorporated by reference herein.

FIELD

The field of the invention generally relates to the field of cytology and histology. More specifically, the field of the invention relates to filter-based systems used for collecting and applying a cytological specimen to a slide.

BACKGROUND

Cytology is a branch of biology dealing with the study of the formation, structure, and function of cells. As applied in a laboratory setting, cytologists, cytotechnologists, and other medical professionals make medical diagnoses of a patient's condition based on visual examination of a specimen of the patient's cells. A typical cytological technique is a "pap smear" test, in which cells are scraped from a woman's cervix and analyzed in order to detect the presence of abnormal cells—a precursor to the onset of cervical cancer. Cytological techniques are also used to detect abnormal cells and disease in other parts of the human body.

Cytological techniques are widely employed because collection of cell samples for analysis is generally less invasive than traditional surgical pathological procedures such as biopsies, whereby a tissue specimen is excised from the patient using specialized biopsy needles having spring loaded translatable stylets, fixed cannulae, and the like. Cell samples may be obtained from the patient by a variety of techniques including, for example, by scraping or swabbing an area, or by using a needle to aspirate body fluids from the chest cavity, bladder, spinal canal, or other appropriate area. The cell samples are placed in solution and subsequently collected and transferred to a glass slide for viewing under magnification. Fixative and staining solutions may be applied to the cells on the glass slide for preserving the specimen for archival purposes and for facilitating examination.

It is generally desirable that the cells on the slide have a proper spatial distribution, so that individual cells can be examined. A monolayer of cells is typically preferred. Accordingly, preparing a specimen from a fluid sample containing many cells typically requires that the cells first be separated from each other by mechanical dispersion, fluidic shear, or other techniques so that a thin, monolayer of cells can be collected and deposited on the slide. In this manner, the cytotechnologist can more readily discern abnormal cells. The cells are also able to be counted to ensure that an adequate number of cells have been evaluated.

Certain methods and apparatus for generating a thin monolayer of cells on a biological slide advantageous for visual examination are disclosed in U.S. Pat. Nos. 5,143,627, 5,240,606, 5,269,918, and 5,282,978, the disclosures of which are expressly incorporated herein by reference.

Two commercially successful apparatus manufacturing in accordance with the teachings of one or more of these patents has been marketed as the ThinPrep™ 2000 and ThinPrep™ 3000 Processors (the "ThinPrep™ Processor") by Cytyc Corporation, located in Boxborough, Mass. During this commercial process, a gynecologic sample is collected using a broom-type or cytobrush/spatula cervical sampling device. Then, the sampling device is rinsed into a vial containing PreservCyt® transport medium. The sample vial is then capped, labeled, and sent to a laboratory for slide preparation. At the laboratory, the vial is placed into the ThinPrep™ Processor, which under control of the instrument's microprocessor, performs the following procedures.

First, the ThinPrep™ Processor uses a portable sample collection device to disperse and collect cells from the liquid sample contained within the sample vial. The sample collection device comprises a disposable plastic filter cylinder, which is introduced by the ThinPrep™ Processor into the liquid sample, and a non-disposable filter plug, which the ThinPrep™ Processor uses to interface with the filter cylinder. The filter plug holds the filter cylinder in an air-tight connection to the ThinPrep™ Processor's pneumatic network for the purpose of collecting cells from the liquid sample. FIGS. 1A and 1B illustrate a conventional filter plug 10 used in connection with the ThinPrep™ Processor. The filter plug 10 is a reusable component that is inserted into a filter cylinder 12 that contains a membrane 14 at one end thereof. A seal is formed between the filter plug 10 and the inner surface of the filter cylinder 12 using an o-ring 16 that is located within a groove 18 of the filter plug 10. The o-ring 16 is compressed to form the sealing engagement with the filter cylinder 12. In order to obtain the cell samples, the ThinPrep™ Processor generates a negative pressure pulse that draws fluid through the filter plug 10 (in the direction of arrow A in FIG. 1B), and collects a thin, even layer of diagnostic cellular material on the filter membrane 14. The ThinPrep™ Processor constantly monitors the rate of flow through the sample collection device during the collection process to prevent the cellular presentation from being too scant or too dense. The ThinPrep™ Processor then generates a positive pressure pulse that deposits the cellular material on a glass slide. The slide is then analyzed to determine whether the sample is positive or negative for a specified disease.

In the filter plug 10 illustrated in FIGS. 1A and 1B, as the filter plug 10 is inserted into the filter cylinder 12, a compression force is immediately placed on the o-ring 16. While this compression force is ultimately needed for the proper seal between the filter plug 10 and the filter cylinder 12, the immediate frictional forces between the o-ring 16 and the interior of the filter cylinder 12 place extra burdens on the insertion and extraction force requirements for the filter plugs 10. In addition, the immediate frictional forces may cause the o-ring 16 to roll or twist, which may result in an incomplete seal being formed. The frictional engagement or rubbing contact between the o-ring 16 and the filter cylinder 12 in filter plugs 10 of the type illustrated in FIGS. 1A and 1B also cause wear on the o-ring 16 which may also result in an incomplete seal. A partial or incomplete seal is, of course, problematic because of the potential for cross-contamination between samples resulting from fluid and/or debris buildup on the filter plug 10.

SUMMARY

Embodiments of the invention provide a filter plug device that forms an airtight seal between the filter plug and the filter cylinder, while minimizing or eliminating frictional rubbing between the filter plug and the filter cylinder during the insertion and extraction process.

In one embodiment, a system for collecting a biological sample includes a collection device comprising a cylindrical body having a bore extending there through and a filter membrane disposed at one end thereof, a filter plug having an insert configured for insertion into the bore, a collar concentrically mounted about the exterior surface of the insert and configured for insertion into the bore, and a gasket disposed about the exterior surface of the insert, wherein an outer dimension of the gasket is variable in response to relative movement between the collar and the insert, and wherein the gasket has a cross section with two end portions and a mid portion that is located radially further away from the insert than the two end portions.

In another embodiment, a system is provided for the releasable engagement with a collection device. The collection device is configured to collect a biological sample and includes a cylindrical body having a bore extending therethrough and a filter membrane disposed at one end thereof. The system further includes a filter plug having an insert configured for insertion into the bore, the filter plug further including a collar concentrically mounted about the exterior surface of the insert and configured for insertion into the bore, the filter plug further including first and second o-rings disposed in a variable width groove formed between the distal end of the insert and the distal tip of the collar.

In another embodiment, a system is provided for releasable engagement with a collection device configured to collect a biological sample. The system includes a collection device having a cylindrical body with a bore extending therethrough and a filter membrane disposed at one end. The system further includes a filter plug configured for releasable engagement within the bore of the collection device. The filter plug has an insert configured for insertion into the bore, the insert including a passageway therein adapted for fluid communication with the bore of the collection device, the insert including a beveled abutment disposed on an exterior surface of the insert at a distal end thereof. The filter plug also has a collar concentrically mounted about the exterior surface of the insert and configured for insertion into the bore, the collar including a beveled tip disposed at an end thereof. First and second o-rings are disposed about the exterior surface of the insert and proximal with respect to the beveled abutment.

In yet another embodiment, a method of releasably securing a filter plug to a collection device includes providing a collection device comprising a cylindrical body having a bore extending therethrough and a filter membrane disposed at one end thereof. A filter plug is provided that has an insert configured for insertion into the bore, the filter plug further including a collar concentrically mounted about the exterior surface of the insert and configured for insertion into the bore, the filter plug further includes first and second o-rings disposed in a variable width groove formed between the distal end of the insert and the distal tip of the collar. The filter plug is inserted into the bore of the collection device. The insert is moved proximally relative to the collar so as to expand the first and second o-rings in a radial direction to engage an inner surface of the cylindrical body. The insert is moved distal relative to the collar so as to disengage the filter plug from the collection device.

BRIEF DESCRIPTION OF THE DRAWINGS

The drawings illustrate the design and utility of embodiments of the invention, in which similar elements are referred to by common reference numerals. In order to better appreciate the advantages and objects of the invention, reference should be made to the accompanying drawings that illustrate the embodiments. The drawings, however, depict the embodiments, and should not be taken as limiting the scope of the invention. With this caveat, the embodiments will be described and explained with additional specificity and detail through the use of the accompanying drawings in which.

DETAILED DESCRIPTION OF THE ILLUSTRATED EMBODIMENTS

Figure 1A:
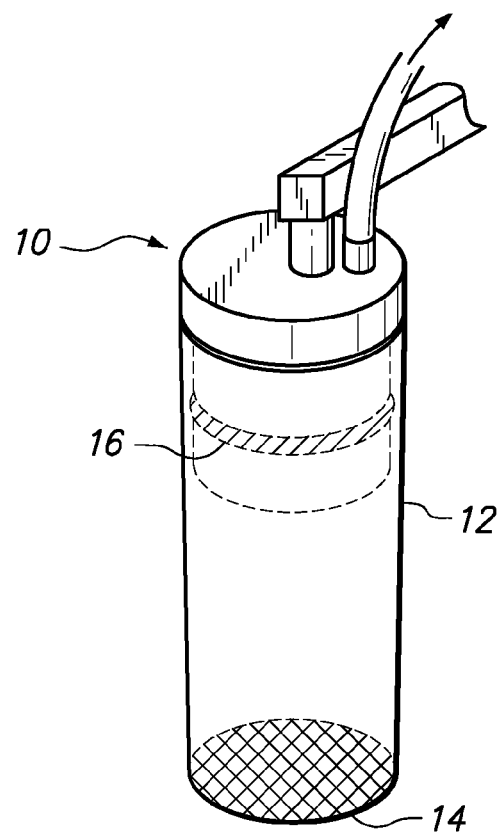
FIG. 1A illustrates a perspective view of a filter plug according to the prior art.
Figure 1B:
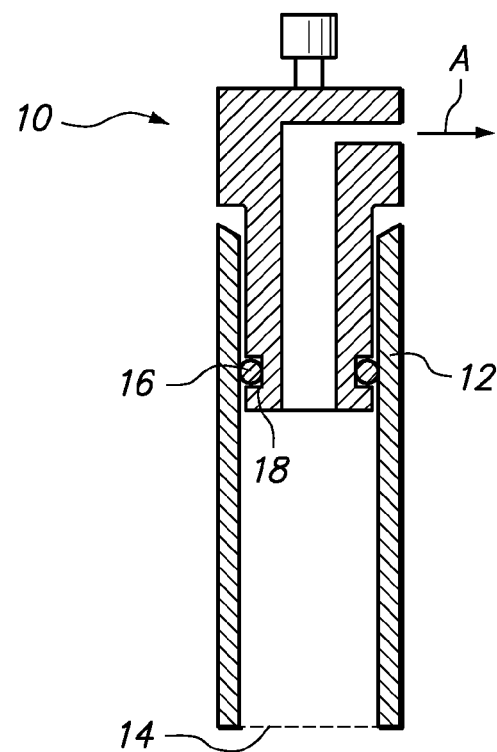
FIG. 1B illustrates a cross-sectional view of the filter plug shown in FIG. 1A.

Various embodiments are described hereinafter with reference to the figures. It should be noted that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated.

Figure 2A:
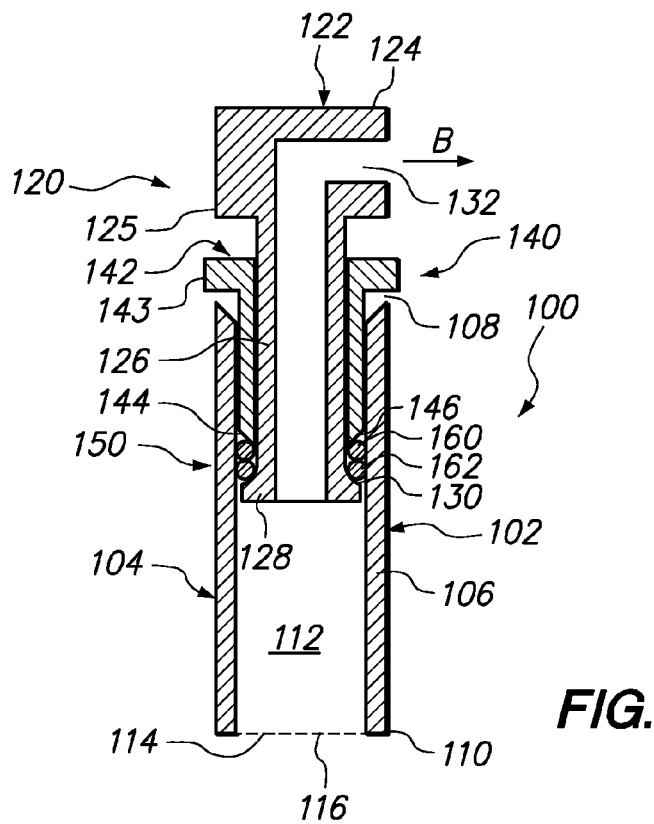
FIG. 2A illustrates a side cross-sectional view of a device for forming a releasable seal with a collection device according to some embodiments.

FIG. 2A illustrates a system 100 for the releasable engagement with a collection device 102 according to some embodiments. The collection device 102 is configured to collect a biological sample, for example, a layer of cells. The collection device 102 illustrated in FIGS. 2A and 2B includes an elongate cylindrical body 104 having a cylindrically-shaped wall 106 with a proximal rim 108 and a distal rim 110. A bore 112 extends longitudinally within the cylindrical wall 106 between the proximal and distal rims 108, 110. The cylindrical wall 106 may be composed of any suitable material, but preferably is composed of a relatively inexpensive biologically inert material such as polystyrene, plastic, or the like. The collection device 102 is typically disposable.

The collection device 102 further includes a filter membrane 114 that is mounted to the distal rim 110 of the cylindrical body 104. The filter membrane 114 includes a number of pores 116 or the like that are in fluid communication with the bore 112. The filter membrane 38 can be mounted to the distal rim 110 in any suitable manner, including thermal bonding, ultrasonic bonding, or solvent bonding. The filter membrane 114 can be composed of a polycarbonic film having a porosity selected for collecting particles of a particular size from the liquid sample. For example, the pore size can be approximately 0.2 to 20 microns. One such membrane is a polycarbonate membrane marketed by Nuclepore Corporation in Pleasanton, Calif. Other filter membranes can be formed from materials including cellulose, nylon, polyester, Polytetrafluoroethylene (PTFE or Teflon®), or any other suitable material. The filter membrane 114 is preferably disposed on the distal rim 110 of the cylindrical wall 106 in a planar fashion, such that the cytological material that has been collected on the filter membrane 114 can be efficiently transferred to the slide as a monolayer of cells. Further details regarding the construction and use of such filters are disclosed in U.S. Pat. Nos. 5,364,597, 5,772,818, and 5,942,700, the entire disclosures of which are expressly incorporated by reference herein.

The reversible sealing system 100 further includes a filter plug 120 that is configured for insertion into the collection device 102. In particular, the filter plug 120 is a reusable component of the system 100 and is used to selectively engage/disengage with a plurality of different collection devices 102 during sample processing. The filter plug 120 includes an insert 122 that is configured for insertion into the bore 112 of the collection device 102. The insert 122 includes a proximal end 124, an elongate cylindrical portion 126 that terminates at a distal end 128. The proximal end 124 may include a flanged portion 125 that extends radially outward and limits (at least in the distal direction) longitudinal movement of the insert 122 into the collection device 102. The distal end 128 includes a beveled abutment 130 that extends radially outward from the insert 122. In this regard, the beveled abutment 130 has an outer diameter that is larger than the outer diameter of the cylindrical portion 126 of the insert 122. While the outer diameter of the beveled abutment 130 is larger than the cylindrical portion, it is still less than the inner diameter of the cylindrical body 104. The beveled abutment 130 may be formed as an angled surface, ramp, or rim that circumscribes the exterior of the insert 122 at the distal end 128.

Figure 2B:
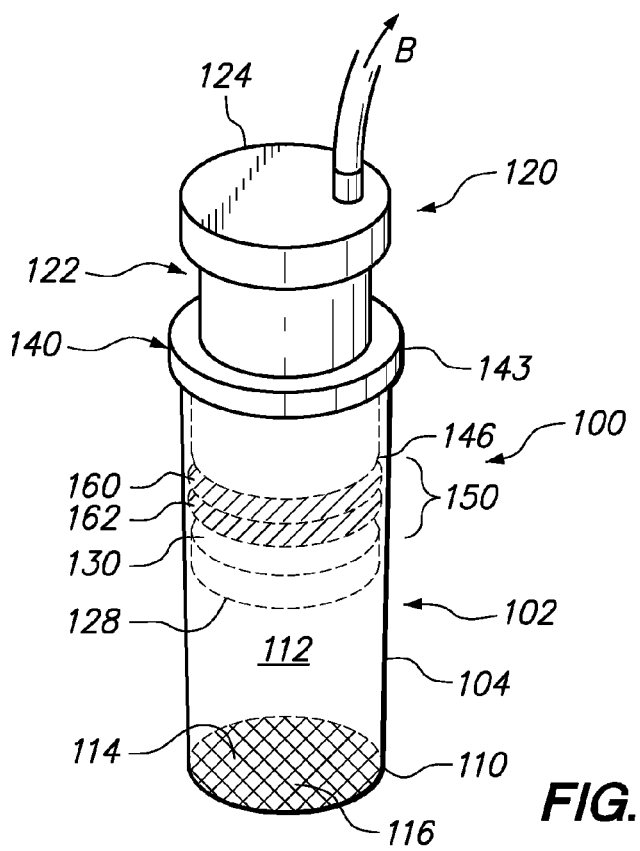
FIG. 2B illustrates a perspective view of a device similar to that illustrated in FIG. 2A.

The insert 122 further includes a bore 132 or other passageway that extends the length of the insert 122 and provides access to the bore 112 of the collection device 102. In this regard, the filter plug 120 may be coupled to a source of negative or positive pressure to collect cellular material on the filter membrane 114 and subsequently transfer the same to a slide (not shown). Arrow(s) B in FIGS. 2A and 2B illustrate the direction of flow when a negative pressure is applied to the filter plug 120. By application of a negative pressure pulse, a monolayer of cells can be formed against the filter membrane 114 as explained herein.

Referring to FIGS. 2A and 2B, the filter plug 120 further includes a collar 140 that is concentrically mounted about the exterior surface of the insert 122. As best seen in FIG. 2A, the collar 140 is dimensioned to fit around the cylindrical portion 126 of the insert 122. In addition, the collar 140 is dimensioned for insertion into the bore 112 of the collection device 120. In this regard, the outer diameter of the collar 140 is less than the internal diameter of the bore 112. As explained herein, the collar 140 and insert 122 are dimensioned to permit sliding movement between the insert 122 and the collar 140 for the engagement/disengagement process.

The collar 140 includes a proximal end 142 and a distal end 144. The proximal end 142 may include a flanged portion 143 that limits movement of the collar 140 longitudinally within the bore 112. The distal end 144 includes a beveled tip 146 that is formed from an angled or ramped surface. When the collar 140 is mounted about the exterior of the insert 122, a variable width groove 150 (best seen in FIGS. 3A and 3B) is created between the beveled tip 146 on the collar 140 and the beveled abutment 130 disposed on the distal end 128 of the insert 122. The width of the groove 150 may be made larger by moving the insert 122 distally with respect to the collar 140. Conversely, the width of the groove 150 may be made smaller by moving the insert 122 proximally with respect to the collar 140. The respective angles of the beveled tip 146 and the beveled abutment 130 are preferably substantially the same, resulting in a generally symmetrical, though variable width groove 150. This aspect may be seen, for example, in FIGS. 3A and 3B.

Figure 3A:
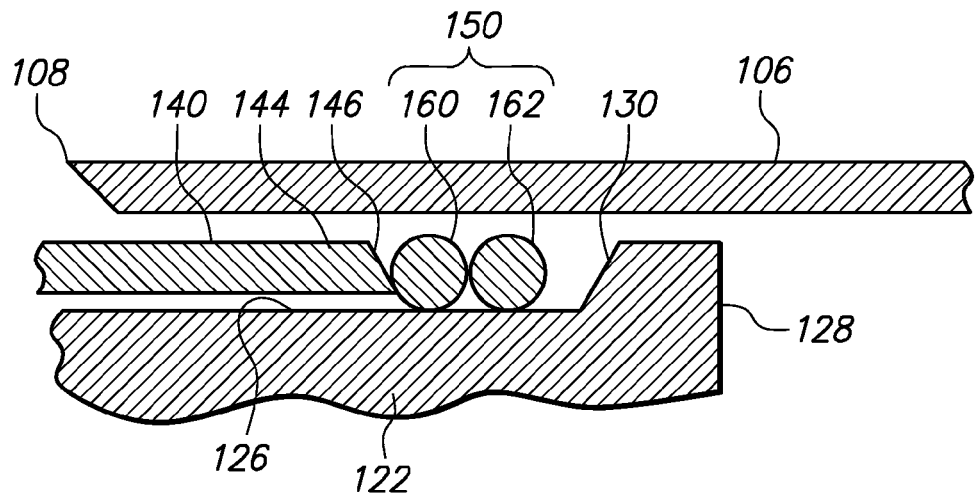
FIG. 3A illustrates a cross-sectional view of the interface between the filter plug and the collection device when the filter plug is in a non-actuated or disengaged state.

Still referring to FIGS. 2A and 2B, first and second o-rings 160, 162 are positioned within the variable width groove 150. The first and second o-rings 160, 162 are disposed about the exterior surface of the cylindrical portion 126 of the insert 122. In one aspect of the embodiments, as illustrated in FIG. 3A, the outer diameters of the first and second o-rings 160, 162 are less than the internal diameter of the cylindrical body 104. Namely, as seen in FIG. 3A, the filter plug 120 may be inserted into the bore 112 of the collection device 102 without either the first or second o-rings 160, 162 frictionally engaging the interior surface of the wall 106. The first and second o-rings 160, 162 may be made of conventional polymeric or elastomeric materials typically used for o-rings.

Figure 3B:
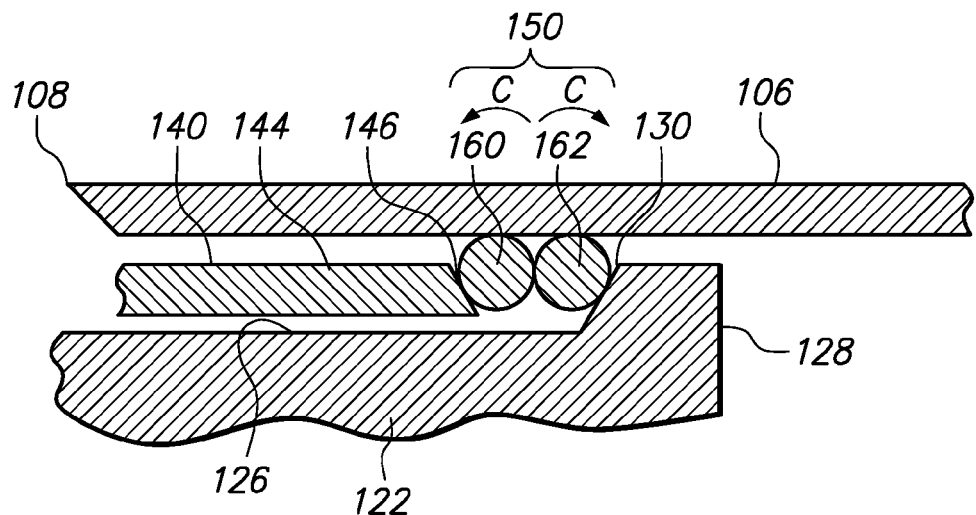
FIG. 3B illustrates a cross-sectional view of the interface between the filter plug and the collection device when the filter plug is in an actuated or engaged state. The two o-rings expand outwardly in response to engagement with ramps and compress against the inner surface of the collection device to form an airtight seal between the filter plug and the collection device.

FIGS. 3A and 3B illustrate partial cross-sectional views of the interaction between the filter plug 120 and the wall 106 of the collection device 102. FIG. 3A illustrates the filter plug 120 in a disengaged state. Namely, the first and second o-rings 160, 162 are snugly positioned about the cylindrical portion 126 of the insert 122. In this manner, the first and second o-rings 160, 162 do not frictionally engage the inner surface of the cylindrical body wall 106. Because of this, there are no additional insertion forces experienced by the filter plug 120 as the same is inserted into the collection device 102.

Typically, the filter plug 120 is operatively coupled to an actuator or gripping device (not shown) as part of an automated sample processor. For example, the actuator is able to insert and remove the filter plug 120 within the bore 112 of the collection device 102. Further, in accordance with some embodiments, the actuator is able to move the insert 122 relative to the collar 140 to engage the first and second o-rings 160, 162 with the inner surface of the cylindrical body wall 106. U.S. Patent Application Publication No. 2005-0247646, which is fully incorporated by reference herein, discloses additional details of a sample processor of the type usable with the filter plug 120 described herein.

FIG. 3B illustrates proximal retraction of the insert 122 relative to the collar 140 which narrows or reduces the width of the groove 150 formed between the beveled abutment 130 of the insert 122 and the beveled tip 146 of the collar 140. As the width of the groove 150 decreases by actuation of the insert 122 in the proximal direction, the first and second o-rings 160, 162 roll up the ramped or beveled surfaces of the beveled tip 146 and the beveled abutment 130 the direction of arrow(s) C. The rolling motion imparted to the first and second o-rings 160, 162 cause the same to roll in opposing directions as illustrated. The first and second o-rings 160, 162 continue to roll up their respective ramping surfaces 146, 130 and, as a result, effectuate diameter enlargement. The rolling motion stops as the o-rings 160, 162 firmly seal against the inner surface of the wall 106. This engaged position is shown in FIG. 3B. A substantially airtight seal is thus formed between the filter plug 120 and the collection device 120.

In the above embodiment, the width of the groove 150 is adjusted by proximal retraction of the insert 122. For example, when the filter plug 120 is inserted into the collection device 120, the filter plug 120 is advanced until the flanged portion 143 engages with the proximal rim 108 of the collection device 102. The o-rings 160, 162 are then expanded in the radial direction by proximal retraction of the insert 122. The seal may be broken by moving the insert 122 in the distal direction, thereby causing the O-rings 160, 162 to roll down their respective ramping surfaces on the beveled abutment 130 and beveled tip 146 until the o-rings 160, 162 resume the configuration illustrated in FIG. 3A.

In an alternative embodiment, the collar 140 may be moved in the distal direction relative to the insert 122 to also achieve narrowing of the groove 150. For example, the actuator or gripping device may be configured to move advance the collar 140 distally over the insert 122 to reduced the width of the groove 150 and thus form the sealing engagement between the filter plug 120 and the collection device 102.

The filter plug 120 described herein offers the benefit of reduced insertion and extraction forces because the o-rings 160, 162 do not engage the inner wall of the collection device 120 on insertion or extraction. The sealing arrangement between the O-rings 160, 162 and the collection device 102 is made only after the filter plug 120 has been properly positioned within the collection device 102. This not only reduces frictional rubbing forces between the o-rings 160, 162 and the collection device 120 which may lead to premature wear, it also limits unwanted rolling or twisting of the o-rings 160, 162 as the filter plug 120 is inserted and removed from the collection device 102.

Figure 4:
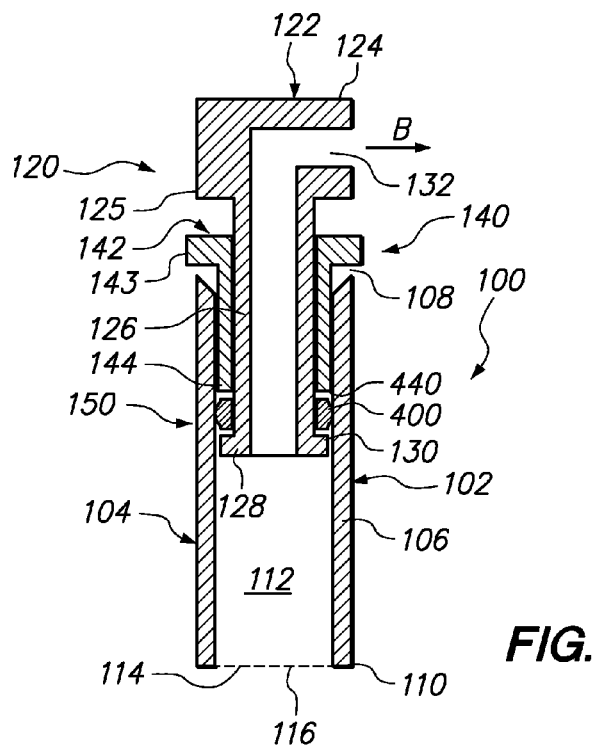
FIG. 4 illustrates a side cross-sectional view of a device for forming a releasable seal with a collection device according to other embodiments, particularly showing the device having a gasket.

In another approach, a gasket may be used instead of the two o-rings 160, 162. FIG. 4 illustrates a variation of the system 100, which includes a gasket 400. As shown in FIG. 4, the variation of the system 100 includes a filter plug 120 having an insert 122 that is dimensioned to fit within the bore 112 of the collection device 102. The insert 122 includes a groove 150 configured to accommodate the gasket 400. During use, the gasket 400 is expanded radially outward to form a seal between the insert 122 and the collection device 102.

Figure 5A:
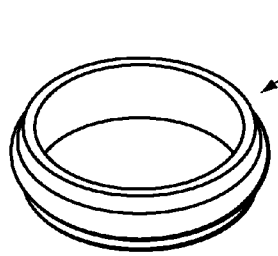
FIG. 5A illustrates a perspective view of the gasket of FIG. 4.
Figure 5B:
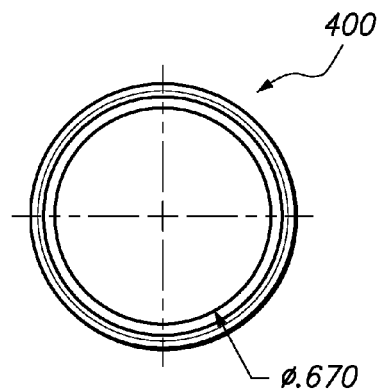
FIG. 5B illustrates an end view of the gasket of FIG. 4.
Figure 5C:
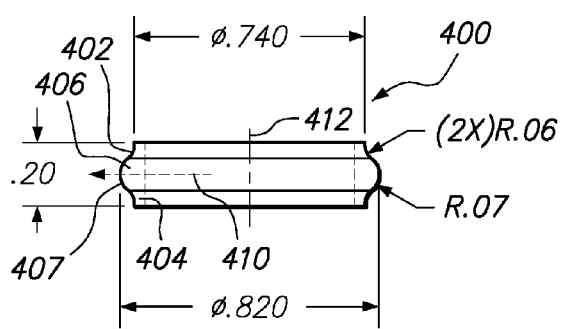
FIG. 5C illustrates a side view of the gasket of FIG. 4.

FIGS. 5A to 5C illustrate the gasket 400 from a perspective view, an end view, and a side view, respectively. As shown in FIG. 5C, the gasket 400 has a cross section with end portions 402, 404, and a mid portion 406, wherein the mid portion 406 has an exterior surface 407 that is disposed further away from the axis 412 than the end portions 402, 404 (i.e., in the radial direction 410). Such configuration allows the mid portion 406 of the gasket 400 to make contact with the inner surface of wall 106 of the collection device 102 during use. Also, such configuration is advantageous in that it provides additional torsional rigidity for the gasket 400, and may prevent the gasket 400 from twisting and/or rolling over during use of the system 100. In addition, unlike the o-rings 160, 162 of FIG. 2A, which may include lubrication for preventing the o-rings from sticking to each other during use, the gasket 400 does not need any such lubrication because the gasket 400 has an unity configuration.

Figure 6A:
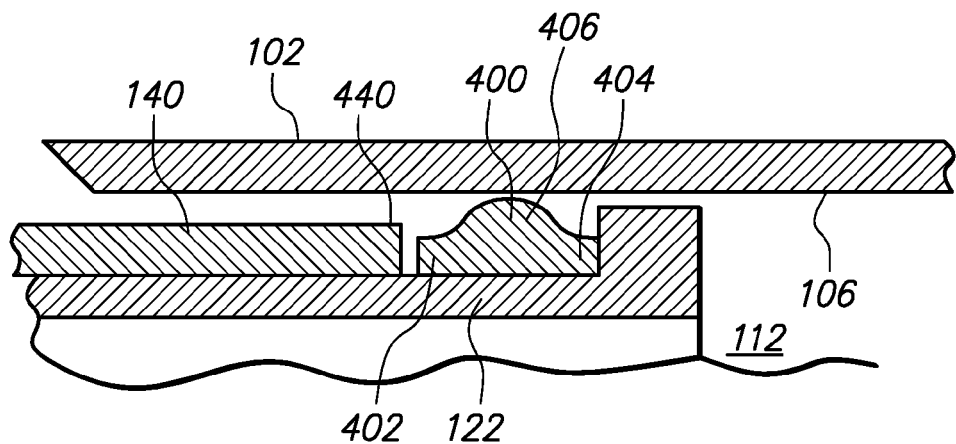
FIG. 6A illustrates a partial side cross-sectional view of the device of FIG. 4, showing the gasket in an unstressed configuration.

FIG. 6A illustrates a partial side cross sectional view of the system 100 of FIG. 4, showing the gasket 400 in an unstressed configuration when it is placed inside the bore 112 of the collection device 102. The gasket 400 has an outer dimension that is smaller than a cross section of the bore 112. Thus, as the gasket 400 is inserted into the bore 112 of the collection device 102, no friction is created between the gasket 400 and the inner surface of the wall 106 of the collection device 102. After the insert 122 with the gasket 400 is inserted into the bore 112 of the collection device 102, the collar 140 is then moved distally relative to the collection device 102 to compress the gasket 400.

Figure 6B:
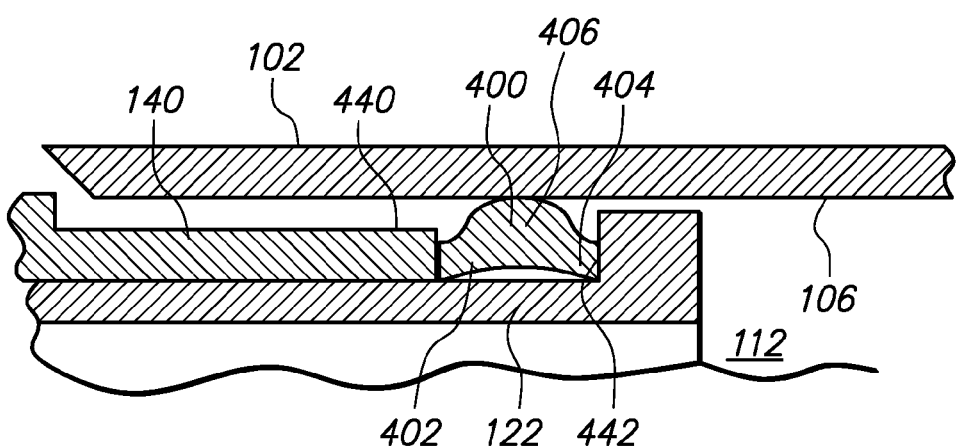
FIG. 6B illustrates a partial side cross-sectional view of the device of FIG. 4, showing the gasket forming a seal.

The collar 140 does not have a beveled tip, but has a blunt tip 440. As the collar 140 is used to compress the gasket 400, the blunt tip 440 at the end 144 of the collar 140 abuts against the end 402 of the gasket 400, while the other end 404 of the gasket 400 abuts against a wall 442 at the end of the insert 122. As a result of the compression on the gasket 400, the gasket 400 expands radially outward in accordance with the poisson's ratio of the material that forms the gasket 400. The expansion presses the gasket 400 against the inner surface of the wall 106 of the collection device 102, thereby forming a seal between the insert 122 and the collection device 102 (FIG. 6B). As illustrated in the embodiments, the cross sectional shape of the gasket 400 is advantageous in that the collar 140 does not need to travel a large distance axially to obtain a large deflection radially outward (where the seal is made). This makes material selection for the gasket 400 easier since the amount of compression by the gasket material does not have to be significant in order to make a good seal. The compression against the gasket 400 also deforms the gasket 400 so that the surface of the gasket 400 facing the insert 122 forms a valley, leaving a space between the gasket 400's inner surface and the insert 122. In other embodiments, instead of moving the collar 140 distally to compress the gasket 400 against the end of the insert 122, the insert 122 may be retracted proximally to compress the gasket 400 against the end of the collar 140.

After the seal is formed, the collection device 102 is then used to pickup, transport, and/or handle filter media. When the process for picking up, transporting, and/or handling the filter media is completed, the collar 140 is retracted to remove the compressive force on the gasket 400. This, in turn, will remove the radially outward force by the gasket 400 towards the inner surface of the wall 106, allowing the gasket 400 to contract back to its unstressed configuration. Since, in its unstressed configuration, the gasket 400's exterior dimension is less than the bore size, the insert 122 with the gasket 400 may be removed from the bore 112 of the collection device 102 without any significant frictional resistance between the gasket 400 and the inner surface of the wall 106 of the collection device 102.

In some embodiments, when the gasket 400 is in an unstressed state, the inner space defined by the gasket 400 has a dimension of 0.67 inch, and the gasket 400 has a thickness (measured along the axis 412) of 0.2 inch. In other embodiments, the gasket 400 can have other dimensions that are different from those described, depending on the size of the system 100.

In any of the embodiments described herein, the gasket 400 may be made from an elastomer, or a liquid silicone rubber, such as LIM®6040 manufactured by General Electric Company, USA. Since liquid silicone rubber has a slippery texture, one benefit of using liquid silicone rubber for the gasket 400 is that it allows the gasket 400 to slide easily against the surface of the insert 122 (such as when the gasket 400 is undergoing deformation due to compression) without any need to add additional lubrication. Another benefit is that such material is chemically compatible with the use of the gasket 400 in the system 100, since it withstands well to the chemicals (such as alcohol) involved in the use of the system 100. However, in other embodiments, the gasket 400 may be made from other materials.

The gasket 400 described herein may have a material hardness of at least 30 durometer Shore A, and more preferably, at least 40 durometer Shore A. In other embodiments, the hardness of the material for the gasket 400 may have other values, such as, less than 40 durometer or less than 30 durometer. In some embodiments, the gasket 400 is made from a 40 durometer Shore A liquid silicone rubber. Such material allows the gasket 400 to be used many of times, and provides a long life cycle for the system 100. In some cases, as long as 20% compression (i.e., 20% strain, or 20% of the maximum compression force) or less is imposed on the gasket 400, the gasket 400 may be used for many thousands of cycles before having to be replaced.

Figures 7A, 7B, 7C:
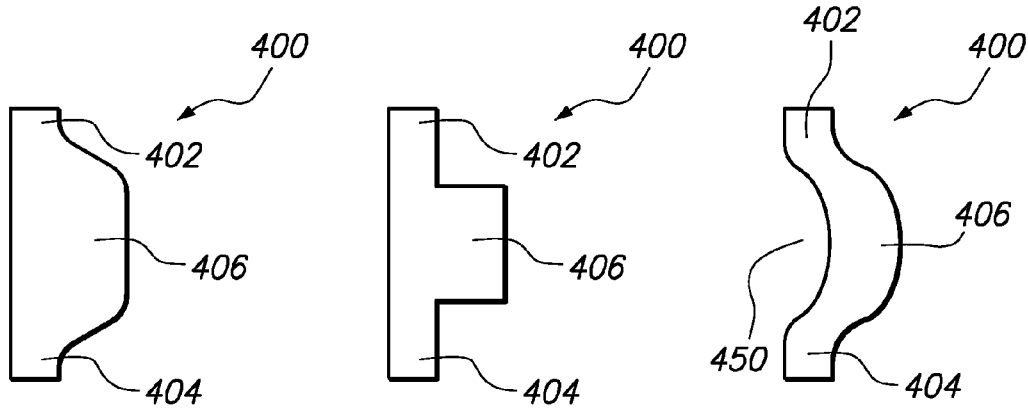
FIGS. 7A to 7C illustrate different variations of the gasket of FIG. 4.

In the above embodiments, the gasket 400 is illustrated as having a curvilinear exterior surface 451 with a bell-shaped profile. In other embodiments, the gasket 400 may have other configurations. FIGS. 7A to 7C show variations of the gasket 400 that may be used with the system 100 of FIG. 4.

As shown in FIG. 7A, the gasket 400 may be provided with a mid portion 406 that is larger (measured along the axis 412) than that shown in the embodiment of FIG. 4, which allows the gasket 400 to form a more tight and reliable seal.

As shown in FIG. 7B, the gasket 400 may be provided with a more abrupt transition between the end portions 402, 404 and the mid portion 406. Thus, the gasket 400 is not limited to having a curvilinear exterior surface as shown in FIG. 5C.

FIG. 7C illustrates another variation of the gasket 400, which is provided with a recess 450 disposed circumferentially on its inner surface facing towards the groove 150 of the insert 122. The recess 450 allows the end portions 402, 404 to be compressed towards each other more easily. In such cases, the radial expansion of the gasket 400 may be due to the poisson's ratio effect as well as the mechanical behavior resulted from the bending action of the end portions 402, 404 relative to the remaining part of the gasket 400. In some cases, the recess 450 also allows the mid portion 406 to be more easily compressed towards the insert 122 during use.

Figure 8:
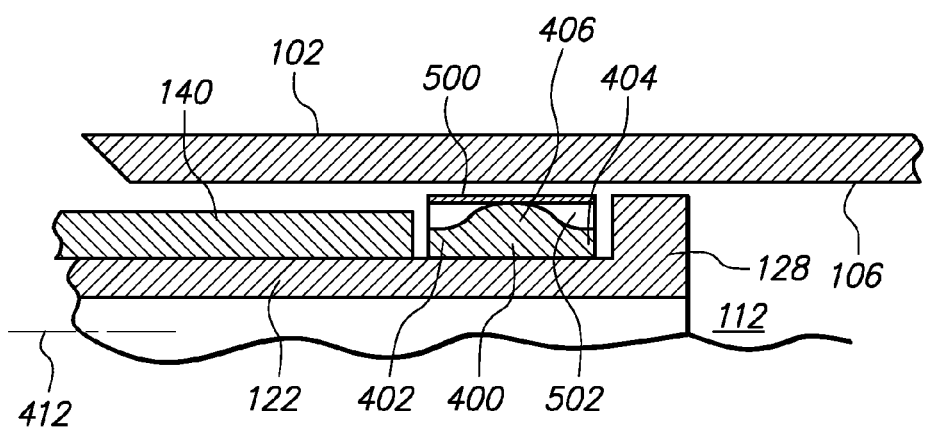
FIG. 8 illustrates a variation of the device of FIG. 4.

In other embodiments, the system 100 may further include a tube 500 surrounding the gasket 400, as shown in FIG. 8. The tube 500 has an opening 502, through which the insert 122 is placed. The tube 500 is disposed over the exterior surface of the gasket 400. During use, the tube 500 occupies part of the space that is between the gasket 400 and the wall 106 of the collection device 102, thereby reducing the amount of radial expansion that the gasket 400 needs to go through in order to form a seal. This in turn translate to reducing the amount of compression that needs to be applied to the gasket 400 (by the end of the collar 140, or by the end of the insert 122) in order to form a seal. Since, with such configuration, the gasket 400 does not have to work as hard to form the seal, the gasket 400 may be used more number of times before it reaches an end of its duty cycle.

As illustrated in FIG. 8, the tube 500 has a length that is the same as the length of the gasket 400 measured in the direction of the axis 412. In other embodiments, the tube 500 may have a length that is shorter or longer than that of the gasket 400. For example, the tube 500 may cover only the mid portion 406 of the gasket 400 in other embodiments. In further embodiments, the tube 500 may cover the mid portion 406 of the gasket 400, as well as part of the distal end 128 of the insert 122. Such feature allows the tube 500 to retain the gasket 400 within the groove 150 of the insert 122. It should be noted that in any of the embodiments described herein, the gasket 400 may be configured (e.g., through a proper selection of material, gasket size, and/or shape) so that little force is required to be applied by the collar 140 (or the insert 122) in order to cause the collar 140 to expand significantly outward in a radial direction.

While embodiments have been shown and described, various modifications may be made without departing from the scope of the present invention. The invention, therefore, should not be limited, except to the following claims, and their equivalents.

What is claimed is:

1. A system for collecting a biological sample, comprising:
a collection device comprising a cylindrical wall defining a bore extending therethrough and a filter membrane disposed at one end thereof;
a filter plug having a cylindrical insert sized and configured for insertion into the bore of the collection device, the filter plug having a flanged proximal end extending radially outward from an exterior surface of the filter plug insert;
a cylindrical collar concentrically mounted about, and movable relative to, the exterior surface of the filter plug insert, the collar sized and configured for insertion into an annular space defined by the exterior surface of the filter plug insert and an interior surface of the collection device; and
a compressible annular gasket disposed about the exterior surface of the filter plug insert between a proximal end of the collar and the flanged proximal end of the filter plug insert, such that movement of the collar towards the flanged proximal end of the filter plug insert compresses and expands the gasket radially outward from the exterior surface of the filter plug insert, so as to form a seal between and thereby engage the the filter plug insert to the collection device.

2. The system of claim 1, the gasket having an outer surface with a bell-shaped cross-sectional profile when in a non-compressed state.

3. The system of claim 1, wherein the filter plug insert and collar are moveable with respect to one another to form a variable width groove between the flanged proximal end of the insert and the proximal end of the collar, the gasket being disposed in the groove.

4. The system of claim 1, wherein the proximal end of the collar comprises a blunt end.

5. The system of claim 1, wherein the collar comprises a flanged end at a proximal end thereof, the flanged end dimensioned to limit movement of the collar within the bore of the collection device.

6. The system of claim 1, wherein the insert has a groove for accommodating the gasket.

7. The system of claim 6, wherein the gasket has a surface facing the insert, and a recess formed at the surface.

8. The system of claim 1, wherein the gasket is made from a liquid silicone rubber.

9. The system of claim 1, wherein the gasket is made from a material having a hardness of at least 30 durometer.

* * * * *